US00PP25087P2

(12) United States Plant Patent
Nishikawa

(10) Patent No.: US PP25,087 P2
(45) Date of Patent: Nov. 18, 2014

(54) ***BIDENS* PLANT NAMED 'FLORBIKANO'**

(50) Latin Name: *Bidens triplinervia*
Varietal Denomination: Florbikano

(76) Inventor: Koichiro Nishikawa, Okayama-ken (JP)

( * ) Notice: Subject to any disclaimer, the term of this patent is extended or adjusted under 35 U.S.C. 154(b) by 184 days.

(21) Appl. No.: 13/507,488

(22) Filed: Jul. 3, 2012

(51) Int. Cl.
*A01H 5/00* (2006.01)

(52) U.S. Cl.
USPC ..... Plt./410

(58) Field of Classification Search
CPC ..... A01H 5/025; A01H 5/02
USPC ..... Plt./410
See application file for complete search history.

*Primary Examiner* — June Hwu
(74) *Attorney, Agent, or Firm* — C. A. Whealy

(57) ABSTRACT

A new and distinct cultivar of *Bidens* plant named 'Florbikano', characterized by its upright, outwardly spreading to trailing and mounding plant habit; vigorous growth habit; freely branching habit; freely flowering habit; long flowering period; inflorescences with yellow orange and dark orange bi-colored ray florets and bright yellow-colored disc florets; and strong peduncles that hold the inflorescences above and beyond the foliar plane.

2 Drawing Sheets

Botanical designation: *Bidens triplinervia.*
Cultivar denomination: 'FLORBIKANO'.

BACKGROUND OF THE INVENTION

The present invention relates to a new and distinct cultivar of *Bidens* plant, botanically known as *Bidens triplinervia* and hereinafter referred to by the name 'Florbikano'.

The new *Bidens* plant is a product of a planned breeding program conducted by the Inventor in Okayama-ken, Japan. The objective of the breeding program is to create new freely branching *Bidens* plants with unique inflorescence coloration.

The new *Bidens* plant originated from a self-pollination made by the Inventor in Okayama-ken, Japan in January, 2010 of *Bidens triplinervia* 'K-SAIKA001', not patented. The new *Bidens* plant was discovered and selected by the Inventor as a single flowering plant from within the progeny of the stated self-pollination in a controlled greenhouse environment in Okayama-ken, Japan in May, 2010.

Asexual reproduction of the new *Bidens* plant by vegetative cuttings in a controlled environment in Okayama-ken, Japan since June, 2010 has shown that the unique features of this new *Bidens* plant are stable and reproduced true to type in successive generations.

SUMMARY OF THE INVENTION

Plants of the new *Bidens* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Florbikano'. These characteristics in combination distinguish 'Florbikano' as a new and distinct *Bidens* plant:

1. Upright, outwardly spreading to trailing and mounding plant habit.
2. Vigorous growth habit.

3. Freely branching habit.
4. Freely flowering habit.
5. Long flowering period.
6. Inflorescences with yellow orange and dark orange bi-colored ray florets and bright yellow-colored disc florets.
7. Strong peduncles that hold the inflorescences above and beyond the foliar plane.

Plants of the new *Bidens* differ primarily from plants of the parent, 'K-SAIKA001' in ray floret color as inflorescences of the new *Bidens* have yellow orange and dark orange bi-colored ray florets whereas inflorescences of 'K-SAIKA001' have yellow and subdued orange bi-colored ray florets.

Plants of the new *Bidens* can be compared to plants of *Bidens triplinervia* 'Yellow Charm', not patented. In side-by-side comparisons conducted in Okayama-ken, Japan, plants of the new *Bidens* differed primarily from plants of 'Yellow Charm' in the following characteristics:

1. Plants of the new *Bidens* were larger than plants of 'Yellow Charm'.
2. Plants of the new *Bidens* were more outwardly spreading and trailing than and not as upright as plants of 'Yellow Charm'.
3. Plants of the new *Bidens* had narrower and darker green-colored leaves than plants of 'Yellow Charm'.
4. Plants of the new *Bidens* and 'Yellow Charm' differed in ray floret color as plants of 'Yellow Charm' had solid yellow-colored ray florets.
5. Plants of the new *Bidens* were more high temperature tolerant than plants of 'Yellow Charm'.

BRIEF DESCRIPTION OF THE PHOTOGRAPHS

The accompanying photographs illustrate the overall appearance of the new *Bidens* plant showing the colors as true as it is reasonably possible to obtain in colored reproductions of this type. Colors in the photographs may differ slightly from the color values cited in the detailed botanical description which accurately describe the colors of the new *Bidens* plant.

The photograph on the first sheet comprises a side perspective view of a typical flowering plant of 'Florbikano' grown in a container.

The photograph on the second sheet is a close-up view of typical developing (top) and fully developed (bottom) inflorescences of 'Florbikano'.

DETAILED BOTANICAL DESCRIPTION

The aforementioned photographs and following observations and measurements describe plants grown in 30-cm containers during the late spring in a polyethylene-covered greenhouse in Okayama-ken, Japan and under cultural practices which approximate those generally used in commercial *Bidens* production. During the production of the plants, day temperatures ranged from 20° C. to 30° C. and night temperatures ranged from 5° C. to 10° C. Plants were one year old when the photographs and description were taken. In the following description, color references are made to The Royal Horticultural Society Colour Chart, 2007 Edition, except where general terms of ordinary dictionary significance are used.

Botanical classification: *Bidens triplinervia* 'Florbikano'.

Parentage: Self-pollination of *Bidens triplinervia* 'K-SAIKA001', not patented.

Propagation:

*Type*.—By vegetative cuttings.

*Time to initiate roots, summer*.—About two weeks at about 20° C. to 30° C.

*Time to initiate roots, winter*.—About three weeks at about 10° C. to 15° C.

*Time to produce a rooted young plant, summer*.—About three weeks at about 20° C. to 30° C.

*Time to produce a rooted young plant, winter*.—About four weeks at about 10° C. to 15° C.

*Root description*.—Fine, fibrous; white in color.

*Rooting habit*.—Freely branching; dense.

Plant description:

*Plant and growth habit*.—Upright, outwardly spreading to trailing and mounding plant habit; vigorous growth habit.

*Branching habit*.—Freely branching habit with lateral branches potentially forming at every node.

*Plant height*.—About 30 cm.

*Plant diameter or spread*.—About 100 cm.

*Lateral branches*.—Length: About 10 cm. Diameter: About 1 mm. Internode length: About 10 cm. Strength: Strong, flexible. Texture: Slightly pubescent. Color: Close to 144A.

Foliage description:

*Arrangement*.—Opposite, simple.

*Length*.—About 3.5 cm.

*Width*.—About 2.5 cm.

*Shape*.—Roughly deltoid; pinnatisect.

*Apex*.—Acute.

*Base*.—Acute.

*Margin*.—Deeply incised; laciniate.

*Texture, upper and lower surfaces*.—Smooth, glabrous.

*Venation pattern*.—Pinnate.

*Color*.—Developing leaves, upper surface: Close to 137A. Developing leaves, lower surface: Close to 138A. Fully expanded leaves, upper surface: Close to N137A; venation, close to 137A. Fully expanded leaves, lower surface: Close to 137C; venation, close to N137C.

*Petioles*.—Length: About 9 mm. Diameter: About 4 mm. Texture, upper surface: Sparsely pubescent. Texture, lower surface: Smooth, glabrous. Color, upper and lower surfaces: Close to 146C.

Inflorescence description:

*Appearance*.—Single (daisy) inflorescence form with ray and disc florets; inflorescences positioned above and beyond the foliar plane on strong peduncles; inflorescences face upright to outwardly.

*Flowering habit*.—Freely flowering habit with numerous inflorescences developing per plant.

*Fragrance*.—None detected.

*Natural flowering season*.—Long flowering period, plants flower continuously from spring until the autumn in Japan.

*Inflorescence longevity*.—Inflorescences last about one week on the plant; inflorescences persistent.

*Inflorescence buds*.—Height: About 3 mm. Diameter: About 3 mm. Shape: Ovoid. Color: Close to 151A.

*Inflorescence size*.—Diameter: About 3.5 cm. Depth (height): About 1 cm. Disc diameter: About 4 mm. Receptacle diameter: About 1.2 cm. Receptacle height: About 4 mm. Receptacle color: Close to 144B.

*Ray florets*.—Length: About 1.7 cm. Width: About 1.1 cm. Shape: Ovate. Apex: Emarginate. Base: Obtuse. Margin: Entire. Texture, upper and lower surfaces: Smooth, glabrous. Number of ray florets per inflorescence: About five arranged in a single whorl. Color: When opening, upper surface: Towards the apex, close to N25C; towards the base, close to N34A. When opening, lower surface: Close to 163A. Fully opened, upper surface: Towards the apex, close to 23A; towards the base, close to 34A; with development, color towards the apex becomes closer to 17C and towards the base, close to 168A. Fully opened, lower surface: Close to 163A; with development, color becomes closer to 162A.

*Disc florets*.—Shape: Tubular; apex dentate. Length: About 5 mm. Diameter: About 1 mm. Number of disc florets per inflorescence: About 42. Color, when opening: Apex: Close to 12B. Mid-section: Close to 161A. Base: Close to 145C. Color, fully opened: Apex: Close to 14A. Mid-section: Close to 151A. Base: Close to 145B.

*Phyllaries*.—Quantity per inflorescence: About six in a single whorl. Length: About 3 mm. Width: About 0.6 mm. Shape: Lanceolate. Apex: Acute. Base: Truncate. Margin: Entire. Texture, upper and lower surfaces: Smooth, glabrous. Color, upper and lower surfaces: Close to 137B.

*Peduncles*.—Length, terminal peduncle: About 7 cm. Length, fourth peduncle: About 10.2 cm. Diameter: About 1 mm. Strength: Strong; flexible. Aspect: Upright to outwardly holding inflorescences above and beyond the foliar plane. Texture: Smooth, glabrous. Color: Close to 146A.

*Reproductive organs*.—Androecium: Present on disc florets only. Quantity per disc floret: One. Filament length: About 1.5 mm. Filament color: Close to 145D. Anther shape: Lanceolate. Anther length: About 1.2 mm. Anther color: Close to 200A. Pollen amount: Scarce. Pollen color: Close to 21A. Gynoecium: Present on ray and disc florets. Pistil length: About 7 mm. Style length: About 5 mm. Style color: Close to 145D. Stigma shape: Bi-parted. Stigma color: Close to 15A. Ovary color: Close to 145D.

*Seeds and fruits*.—Seed and fruit development have not been observed on plants of the new *Bidens*.

Disease & pest resistance: Plants of the new *Bidens* have not been shown to be resistant to pathogens and pests common to *Bidens* plants.

Garden performance: Plants of the new Clematis have exhibited good tolerance to rain and wind and have been observed to tolerate temperatures from about 1° C. to about 47° C.

It is claimed:

1. A new and distinct *Bidens* plant named 'Florbikano' as illustrated and described.

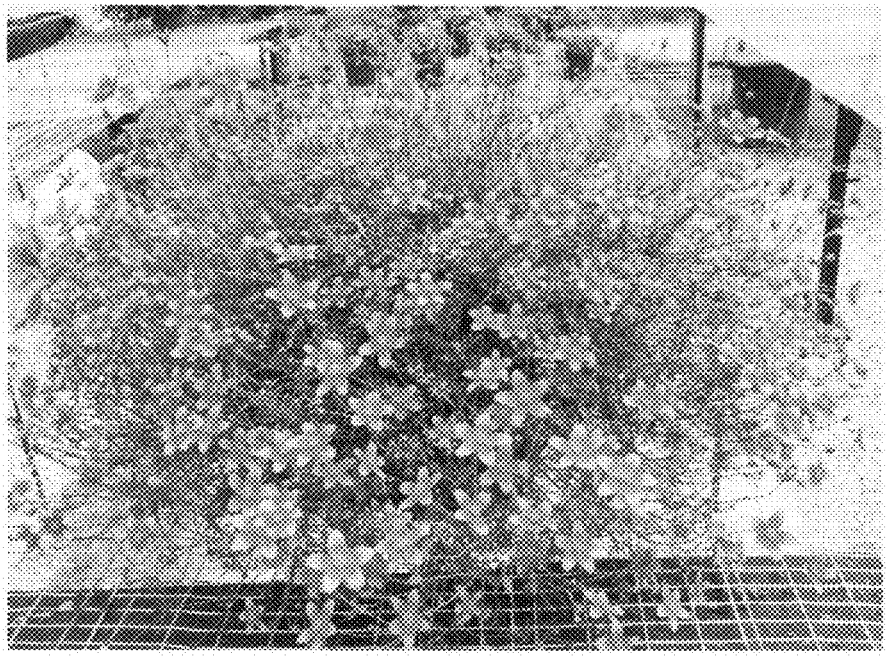

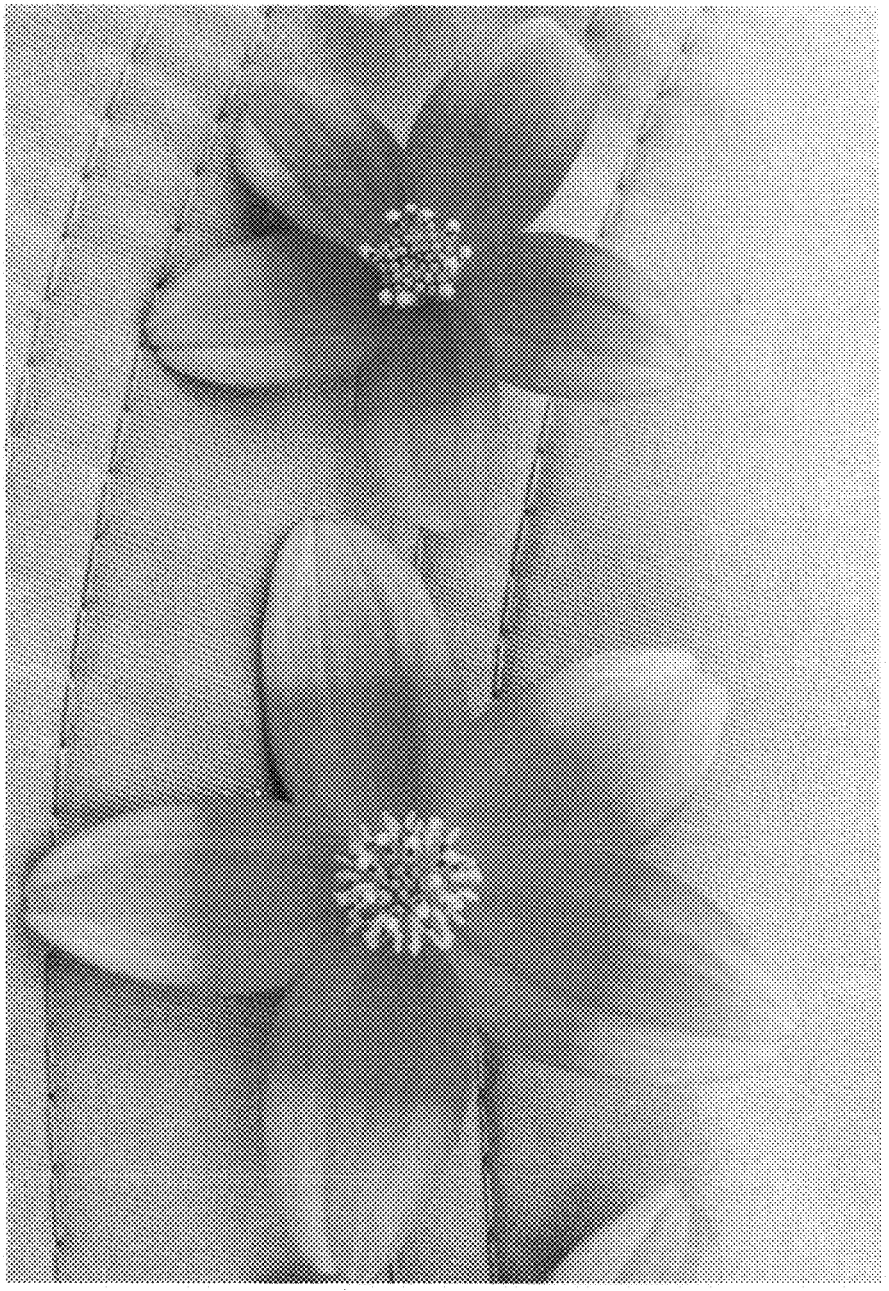

* * * * *